United States Patent
Liu et al.

(10) Patent No.: US 6,310,094 B1
(45) Date of Patent: Oct. 30, 2001

(54) READY-TO-USE ESMOLOL SOLUTION

(75) Inventors: Jie Liu, Scotch Plains; Satish K. Pejaver, Bridgewater; George Owoo, North Plainfield, all of NJ (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/759,547

(22) Filed: Jan. 12, 2001

(51) Int. Cl.[7] ............................................... A61K 31/24
(52) U.S. Cl. ............................................................ 514/538
(58) Field of Search ............................................. 514/538

(56) References Cited

U.S. PATENT DOCUMENTS 4,857,552 * 8/1989 Rosenberg et al. ................. 514/538

* cited by examiner

Primary Examiner—Raymond Henley, III
(74) Attorney, Agent, or Firm—Kenneth E Jaconetty

(57) ABSTRACT

A ready-to-use injectable, aqueous pharmaceutical composition for the treatment of cardiac conditions, comprising methyl-3-[4-(2-hydroxy-3-isopropylamino) propoxy] phenylpropionate hydrochloride (esmolol hydrochloride), a buffering agent and an osmotic-adjusting agent, as well as a method for its manufacture in a container, is disclosed.

9 Claims, No Drawings

READY-TO-USE ESMOLOL SOLUTION

SUMMARY OF THE INVENTION

The present invention relates to a ready-to-use injectable, aqueous pharmaceutical composition for the treatment of cardiac conditions comprising methyl-3-[4-(2-hydroxy-3-isopropylamino propoxy] phenylpropionate hydrochloride (esmolol hydrochloride), a buffering agent and an osmotic-adjusting agent, and further relates to a method for its manufacture in a container.

BACKGROUND OF THE INVENTION

Esmolol hydrochloride is a short-acting beta-blocker used for treatment or prophylaxis of cardiac disorders in mammals. Most of the currently available beta-blockers are stable drugs which can be administered to cardiac patients over relatively long periods of time. However, it is often desirable in the critical care setting to quickly reduce heart work or improve rhythmicity during a cardiac crisis, e.g., during or shortly after a myocardial infarction. Conventional beta-blocking agents can be employed for such treatment, but their long durations of action can cause undesirable side effects.

Esmolol hydrochloride contains an ester functional group and possesses the typical beta-adrenergic blocking activity. However, it differs from conventional beta-blocking compound in that esmolol hydrochloride has a short duration in vivo due to the presence of the ester group. Thus, esmolol hydrochloride is advantageous compared to the conventional beta-blockers because of its unique short-acting activity. However, the ester group in esmolol hydrochloride is found to be unstable in an aqueous environment because of it extreme susceptibility to hydrolytic degradation.

The stability of esmolol in water is mediated by the rate of acid/base hydrolysis of the labile aliphatic methyl ester group. In the past, the rate of degradation of esmolol hydrochloride has been reduced by the use of acetate as a buffer, maintaining the pH as close to 5.0 as possible, minimizing the concentration of esmolol in the solution, and minimizing the concentration of buffer used. Prior art formulations maintain a reasonably long shelf-life, however, they are packaged in glass vials or ampules, and suffer from severe degradation upon autoclaving. As a result, prior art formulations are prepared aseptically. C.f. U.S. Pat. No. 4,857,552. However, terminal sterilization is typically preferred by regulatory authorities as a way of reducing microbiological burden and to ensure the safety of the finished product.

In addition, the formulation disclosed in U.S. Pat. No. 4,857,552 is a small volume injectable formulation. For the purposes of intravenous infusion, the disclosed formulation must be further diluted in pharmaceutically acceptable diluents prior to use. This creates a potential opportunity for calculation or dilution error in a hospital setting. Additionally, microbiological contamination of the product during dilution/aseptic handling is of primary concern. Therefore, there remains a need for a ready-to-use large volume parenteral esmolol hydrochloride that is microbiologically safe and stable in vitro during storage.

DETAILED DESCRIPTION OF THE INVENTION

The present invention provides a stable, ready-to-use parenteral solution containing esmolol hydrochloride and a pharmaceutically acceptable buffering agent and an osmotic adjusting agent to adjust the tonicity of the solution. The solution can be packaged in a sealed container and subjected to terminal sterilization via autoclaving to reduce the microbiological burden of the formulation. Esmolol hydrochloride formulations of the prior art cannot survive autoclaving. The present invention is stable against hydrolytic degradation and other adverse chemical reactions, and possesses a pharmaceutically-acceptable shelf-life. The product is a ready-to-use infusion which can be used directly without requiring any additional procedures for dilution. This avoids the inconvenience of diluting a concentrated esmolol small volume parenteral formulation into infusion diluents prior to infusion along, eliminates the risk of microbiological contamination during aseptic handling and any potential calculation or dilution error. As a result, the present invention enhances patient safety and physician/nurse compliance with use of esmolol injection.

The pH of the composition greatly effects its stability. The pH should be between 3.5 and 6.5, preferably between 4.5 and 5.5, more preferably about 5.0. The pH can be adjusted as known in the art by addition of sodium hydroxide or hydrochloric acid. Esmolol hydrochloride is present in the instant composition in an amount ranging from 0.1–100 mg/ml, preferably 1–10 mg/ml.

Suitable buffering agents are known in the art, and are present in the composition in an amount ranging from 0.1–5.0 mg/ml, preferably 0.4–3.0 mg/ml. Buffering agents include acetate, glutamate, citrate, tartrate, benzoate, lactate, gluconate, phosphate and glycine. The preferred buffering agent is acetate.

Suitable osmotic-adjusting agents are known in the art, and are present in the composition in an amount ranging from 1–10 mg/ml. Osmotic-adjusting agents include sodium chloride, dextrose, sodium bicarbonate, calcium chloride, potassium chloride, sodium lactate, Ringer's solution and lactated Ringer's solution. Preferred are sodium chloride, in an amount ranging from 4–60 mg/ml, more preferably 4–10 mg/ml, and dextrose, in an amount ranging from 25–60 mg/ml. Dextrose is preferably present in the composition of the present invention at a level no greater than 5% (weight by weight) in combination with sodium chloride.

Compositions according to the present invention are packaged in suitable sealed containers, which may be either glass or polymer-based. Polymeric containers are preferably flexible, and can be contain or be free of polyvinylchloride (PVC). Preferred containers are free of PVC, such as those disclosed in U.S. Pat. Nos. 5,849,843 and 5,998,019.

The polymeric containers can further be provided with a moisture barrier as a secondary packaging system to prevent the loss of water during storage and to further ensure the stability of the formulation. A preferred moisture barrier is an aluminum overpouch.

Procedures for filling compositions of the present invention in containers, and their subsequent processing are known in the art. Typical autoclave cycles in the pharmaceutical industry to achieve terminal sterilization of the final product are 121° C. for 15 minutes. The esmolol hydrochloride composition of the present invention can be autoclaved at a temperature ranging from 115 to 130° C. for a period of time ranging from 5 to 40 minutes with acceptable stability. Autoclaving is preferably carried out in the temperature range of 119° C. to 122° C. for a period of time ranging from 20 to 36 minutes.

EXAMPLES

Example 1

The following describes the preparation of ready-to-use infusion bags of the present invention containing 10 mg/ml esmolol HCl solution. The concentration of each ingredient of the composition is as follows:

| Ingredient | Amount/ml Solution |
| --- | --- |
| Esmolol HCl | 11 mg/ml |
| Sodium Chloride (osmotic) | 5.9 mg/ml |
| Sodium Acetate Trihydrate (buffer) | 2.8 mg/ml |
| Glacial Acetic Acid (buffer) | 0.546 mg/ml |
| Sodium Hydroxide/Hydrochloric Acid | pH adjustment to 5.0 |
| Water for Injection, USP | qs |

The equipment and glassware for compounding, filtering, and filling are properly washed and depyrogenated. The filter assembly, filling tube assembly, and other parts and equipment are sterilized.

Eighty percent (80%) of the final volume of cool Water for Injection is collected in a calibrated compounding tank. Sodium chloride is added to the tank and the solution is stirred until sodium chloride is dissolved. Glacial acetic acid and sodium acetate are then added to the tank. The solution is further stirred until all excipients are dissolved. The tank is adjusted to 90% of final volume with Water for Injection and mixed. Approximately 2 liter of this solution (buffer solution) is removed for use in preparation of the slurry solution. Esmolol hydrochloride is weighed and added to the 2 liter of the buffer solution to form a slurry solution. This slurry is then added to the compounding tank and the solution is mixed. The solution is then adjusted to pH 5.0 with 1 N sodium hydroxide or hydrochloric acid. The solution is brought to final volume with Water for Injection and mixed.

The solution is then filled into 250 ml non-PVC flexible bags (IntraVia™ flexible plastic container (PL 2408-3 non-PVC multi-layer plastic film) with one standard PL 146® PVC membrane tube, one PL 2409-3 multi-layer plastic co-extruded administration port tube, one PL 141 PVC blue-tip closure (administration port protector), available from Baxter Healthcare Corporation.) These bags are sealed in aluminum foil overpouches. The products are then loaded into an autoclaving sterilizer and sterilized at 121° C. for 36 minutes.

The sterilized products are subjected to inspection and release tests. The bag products prepared above are selected and placed on stability test. At each stability time, one bag of each solution are tested for pH, potency, osmolality, physical appearance and particulate matter. The concentration of the drug is determined by a high performance liquid chromatographic (HPLC) method. The results are summarized as follows:

| | | | | | Particulate Matter | |
| --- | --- | --- | --- | --- | --- | --- |
| Test Time | Potency (mg/ml) | pH | Osmolality (mosm/kg) | Visual Inspection | Particles ≧10 μm | Particles ≧25 μm |
| 25° C./35% RH* | | | | | | |
| Initial | 10.9 | 4.9 | 304 | Pass** | 0 | 0 |
| 3 months | 10.7 | 4.9 | 303 | Pass | 0 | 0 |
| 6 months | 10.6 | 4.9 | 302 | Pass | 0 | 0 |
| 30° C./35% RH* | | | | | | |
| Initial | 10.9 | 4.9 | 304 | Pass | 0 | 0 |
| 3 months | 10.6 | 4.9 | 304 | Pass | 0 | 0 |
| 6 months | 10.4 | 4.8 | 304 | Pass | 0 | 0 |
| 40° C./15% RH* | | | | | | |
| Initial | 10.9 | 4.9 | 304 | Pass | 0 | 0 |
| 1 months | 10.7 | 4.9 | 304 | Pass | 0 | 0 |
| 2 months | 10.5 | 4.9 | 304 | Pass | 0 | 0 |
| 3 months | 10.4 | 4.9 | 306 | Pass | 0 | 0 |
| 6 months | 9.9 | 4.8 | 308 | Pass | 0 | 0 |

*The storage temperature and humidity conditions. RH = Relative Humidity
**Pass: clear colorless solution.

Example 2

Example 1 is repeated with the following formulation:

| Ingredient | Amount/ml Solution |
| --- | --- |
| Esmolol HCl | 11 mg/ml |
| Dextrose | 50 mg/ml |
| Sodium Acetate Trihydrate | 2.8 mg/ml |
| Glacial Acetic Acid | 0.546 mg/ml |
| Sodium Hydroxide/Hydrochloric Acid | pH adjustment to 5.0 |
| Water for Injection, USP | qs |

Example 3

Example 1 is repeated with the following formulation:

| Ingredient | Amount/ml Solution |
| --- | --- |
| Esmolol HCl | 11 mg/ml |
| Dextrose | 25 mg/ml |
| Sodium Chloride | 2.95 mg/ml |
| Sodium Acetate Trihydrate | 2.8 mg/ml |
| Glacial Acetic Acid | 0.546 mg/ml |

-continued

| Ingredient | Amount/ml Solution |
| --- | --- |
| Sodium Hydroxide/Hydrochloric Acid | pH adjustment to 5.0 |
| Water for Injection, USP | qs |

We claim:

1. An injectable, aqueous pharmaceutical composition for the treatment of cardiac conditions, having a pH between 3.5 and 6.5 and comprising
   a. 0.1–100 mg/ml methyl-3-[4-(2-hydroxy-3-isopropylamino) propoxy] phenylpropionate hydrochloride (esmolol hydrochloride),
   b. 0.1–5.0 mg/ml buffering agent, and
   c. 1–100 mg/ml osmotic-adjusting agent.

2. The composition of claim 1 wherein the buffering agent comprises at least one of acetate, glutamate, citrate, tartrate, benzoate, lactate, gluconate, phosphate and glycine.

3. The composition of claim 1 wherein the osmotic-adjusting agent comprises at least one of sodium chloride, dextrose, sodium bicarbonate, calcium chloride, potassium chloride, sodium lactate, Ringer's solution and lactated Ringer's solution.

4. A method for preparing a sterile, injectable aqueous pharmaceutical composition for the treatment of cardiac conditions, comprising forming an aqueous composition having a pH between 3.5 and 6.5 comprising methyl-3-[4-(2-hydroxy-3-isopropylamino)propoxy] phenylpropionate hydrochloride (esmolol hydrochloride), a buffering agent, and an osmotic-adjusting agent in a sealed container, and autoclaving for a period of time sufficient to render the composition sterile.

5. The method of claim 4 wherein the composition comprises 0.1–100 mg/ml methyl-3-[4-(2-hydroxy-3-isopropylamino) propoxy] phenylpropionate hydrochloride (esmolol hydrochloride), 0.1–5.0 mg/ml buffering agent, and 1–100 mg/ml osmotic-adjusting agent.

6. The method of claim 4 wherein the composition is autoclaved at a temperature ranging from 115 to 130° C. for a period of time ranging from 5 to 40 minutes.

7. The method of claim 4 wherein the container is a flexible polymeric container free from polyvinyl chloride.

8. The method of claim 4 further comprising providing the container with a moisture barrier.

9. The method of claim 8 wherein the moisture barrier is an aluminum overpouch.

* * * * *